(12) United States Patent
Allen et al.

(10) Patent No.: US 10,773,102 B2
(45) Date of Patent: Sep. 15, 2020

(54) RADIOTHERAPY AND IMAGING APPARATUS

(71) Applicant: Elekta AB (publ), Stockholm (SE)

(72) Inventors: John Allen, Haywards Heath (GB);
Duncan Neil Bourne, Redhill (GB);
Kevin Brown, Horsham (GB)

(73) Assignee: Elekta AB (publ), Stockholm (SE)

( * ) Notice: Subject to any disclaimer, the term of this patent is extended or adjusted under 35 U.S.C. 154(b) by 0 days.

(21) Appl. No.: 15/624,433

(22) Filed: Jun. 15, 2017

(65) Prior Publication Data
US 2017/0281973 A1     Oct. 5, 2017

Related U.S. Application Data

(63) Continuation of application No. 12/704,966, filed on Feb. 12, 2010, now Pat. No. 9,694,205.

(51) Int. Cl.
*A61N 5/10*     (2006.01)
(52) U.S. Cl.
CPC ......... *A61N 5/1045* (2013.01); *A61N 5/1042* (2013.01); *A61N 5/1049* (2013.01);
(Continued)
(58) Field of Classification Search
CPC .. A61N 5/1045; A61N 5/1081; A61N 5/1042; A61N 2005/1055
See application file for complete search history.

(56) References Cited

U.S. PATENT DOCUMENTS 4,868,843 A * 9/1989 Nunan ................... G21K 1/046
378/152

5,008,907 A     4/1991 Norman et al.
(Continued)

FOREIGN PATENT DOCUMENTS

WO     03008986 A2     1/2003
WO     05081842 A2     9/2005
(Continued)

OTHER PUBLICATIONS

"Radiation induced currents in MRI RF coils: application to linac/MRI integration" by B. Burke et al. Phys Med Biol. published online: Jan. 13, 2010. pp. 1-19 (Year: 2010).*
(Continued)

*Primary Examiner* — Jeffrey G Hoekstra
*Assistant Examiner* — Jason M Ip
(74) *Attorney, Agent, or Firm* — Schwegman Lundberg & Woessner, P.A.

(57) ABSTRACT

Radiotherapy apparatus comprises a source of radiation mounted on a chassis, the chassis being rotatable about a rotation axis and the source being adapted to emit a beam of radiation along a beam axis that intersects with the rotation axis; a patient support, moveable along a translation axis; a set of magnetic coils located on either side of the beam, for establishing a magnetic field at the point of intersection, spaced from that point along a first direction; the translation axis, the rotation axis, and the first direction being substantially parallel; and further comprising a multi-leaf collimator fixed in its orientation with respect to the source of radiation, the multi-leaf collimator comprising a plurality of elongate leaves disposed with their longitudinal directions substantially aligned with the first direction and movable in that direction between a withdrawn position in which the leaf lies outside the beam.

18 Claims, 6 Drawing Sheets

(52) U.S. Cl.
CPC .... *A61N 5/1081* (2013.01); *A61N 2005/1054* (2013.01); *A61N 2005/1055* (2013.01)

(56) References Cited

U.S. PATENT DOCUMENTS

| | | | |
|---|---|---|---|
| 5,166,531 A * | 11/1992 | Huntzinger | A61N 5/1042 250/505.1 |
| 5,317,616 A | 5/1994 | Swerdloff et al. | |
| 5,438,991 A | 8/1995 | Yu et al. | |
| 6,198,957 B1 | 3/2001 | Green | |
| 6,266,393 B1 * | 7/2001 | Ein-Gal | A61N 5/1042 250/505.1 |
| 6,366,798 B2 | 4/2002 | Green | |
| 6,438,202 B1 | 8/2002 | Olivera et al. | |
| 6,459,769 B1 * | 10/2002 | Cosman | A61N 5/1042 250/505.1 |
| 6,725,078 B2 | 4/2004 | Bucholz et al. | |
| 9,694,205 B2 | 7/2017 | Allen et al. | |
| 2005/0197564 A1 | 9/2005 | Dempsey | |
| 2005/0267350 A1 | 12/2005 | McKinnon | |
| 2006/0067480 A1 | 3/2006 | Juschka et al. | |
| 2006/0182326 A1 | 8/2006 | Schildkraut et al. | |
| 2006/0193411 A1 | 8/2006 | Cadman | |
| 2008/0208036 A1 | 8/2008 | Amies et al. | |
| 2009/0124887 A1 | 5/2009 | Roell et al. | |
| 2011/0201919 A1 | 8/2011 | Allen et al. | |

FOREIGN PATENT DOCUMENTS

| | | | |
|---|---|---|---|
| WO | WO 2008/122899 A1 * | 10/2008 | ............. A61B 5/055 |
| WO | 09155700 A1 | 12/2009 | |

OTHER PUBLICATIONS

European Search Report; dated Apr. 20, 2011.
Raaymakers et al., Integrating a 1.5 T MRI Scanner with a 6 MV Accelerator: Proof of Concept, Physics in Medicine and Biology, vol. 54, 2009, N229-N237.

* cited by examiner

PRIOR
ART

RADIOTHERAPY AND IMAGING APPARATUS

FIELD OF THE INVENTION

The present invention relates to a radiotherapy apparatus and, especially, to a form of multi-leaf collimator suited to certain types of radiotherapy apparatus with imaging devices.

BACKGROUND ART

It is known that exposure of human or animal tissue to ionising radiation will kill the cells thus exposed. This finds application in the treatment of pathological cells, for example. In order to treat tumours deep within the body of the patient, the radiation must however penetrate the healthy tissue in order to irradiate and destroy the pathological cells. In conventional radiation therapy, large volumes of healthy tissue can thus be exposed to harmful doses of radiation, resulting in prolonged recovery periods for the patient. It is, therefore, desirable to design a device for treating a patient with ionising radiation and treatment protocols so as to expose the pathological tissue to a dose of radiation which will result in the death of those cells, whilst keeping the exposure of healthy tissue to a minimum.

Several methods have previously been employed to achieve the desired pathological cell-destroying exposure whilst keeping the exposure of healthy cells to a minimum. Many methods work by directing radiation at a tumour from a number of directions, either simultaneously from multiple sources or multiple exposures from a single source. The intensity of radiation emanating from each direction is therefore less than would be required to actually destroy cells (although still sufficient to damage the cells), but where the radiation beams from the multiple directions converge, the intensity of radiation is sufficient to deliver a therapeutic dose. By providing radiation from multiple directions, the amount of radiation delivered to surrounding healthy cells can be minimized.

The shape of the beam varies. For single-source devices, cone beams centred on the isocentre are common, while fan beams are also employed (for example as shown in U.S. Pat. No. 5,317,616). Both types of beam require collimation apparatus, in order to shape the beam as required and reduce the irradiation of healthy tissue. There are currently two main types of variable-shape collimator which are in use in conventional radiotherapy machines.

The first, more common type of multi-leaf collimator ("MLC") has a number of leaves that can be positioned in substantially continuously variable positions (see FIG. 8). The maximum field size is typically square, and the MLC can be rotated so as to orient the leaf direction optimally with regard to the shape of features on the target. Typically, the patient position is adjusted so that the target is at the centre of the MLC, and thus a high resolution MLC can also be of a small size and positioned centrally. Alternatively, composite resolution collimators have been produced where high resolution (i.e. relatively thin) leaves are provided in the central portion and regular width (i.e. relatively thick) leaves are provided in the outer portions. A lower limit to the thickness of the leaves is imposed by the possibility that they may bend under their own weight. No support can be provided, as this would be incompatible with the field defining lamp that is usually provided, and the alternative electron beam that is offered by most linacs.

Fan beam-based systems typically use a binary collimator; this is shaped as a narrow slit, and has a number of leaves positioned along the slit that are either fully closed or fully open (see FIG. 9). The shape of the field is not adjusted, but the time for which the leaves are opened is varied, thereby controlling the radiation fluence that passes though the slit. Due to the slit nature of the collimator, this is used in conjunction with longitudinal motion of the patient so as to cover the extent of the target transverse to the slit.

SUMMARY OF THE INVENTION

We have realised that there are distinct advantages in applying a multi-leaf collimator (as opposed to a binary collimator) to a narrow-window single source radiotherapy device. This will be particularly useful in the context of a radiotherapy device equipped with an MRI functionality; such a device may have a narrow field of view in order to allow for the MRI coils either side of the beam. Such a device will also need excellent collimation, as the MRI system will require the radiation source to be at a larger distance from the target—so a conventional collimator would have a larger penumbra and the projected leaf thickness at the target will be larger.

A binary collimator would be a comparably inefficient method of delivering radiation in such an arrangement. The effective dose rate of a combined MRI/linac is already reduced by the increased distance of the radiation source from the target and attenuation due to the material of the magnet. A binary collimator depends on a high dose rate to produce an acceptable delivery time, making it incompatible with the limited dose rate of an MRI Linac. In addition, an MRI/Linac is ideally suited to treat moving targets, due to its ability to image the target motion simultaneously with irradiating the target. A binary collimator is not ideal for target tracking applications due to its use of temporal modulation instead of spatial modulation.

The present invention therefore provides a radiotherapy apparatus comprising a source of radiation mounted on a chassis, the chassis being rotatable about a rotation axis and the source being adapted to emit a beam of radiation along a beam axis that intersects with the rotation axis; a patient support, moveable along a translation axis; a set of magnetic coils located on either side of the beam, for establishing a magnetic field at the point of intersection, spaced from that point along a first direction; the translation axis, the rotation axis, and the first direction being substantially parallel; and further comprising a multi-leaf collimator fixed in its orientation with respect to the source of radiation, the multi-leaf collimator comprising a plurality of elongate leaves disposed with their longitudinal directions substantially aligned with the first direction and movable in that direction between a withdrawn position in which the leaf lies outside the beam, an extended position in which the leaf projects across the beam and a plurality of intermediate positions therebetween.

Two banks of leaves can be provided, extending from each side of the beam towards the centre.

Leaf guides can be provided, extending across the beam, along at least one of which each of the leaves slides. In this way, thinner leaves can be provided than is normally the case. Given that the radiotherapy apparatus is irradiating through an otherwise opaque magnet there is no purpose in providing a field defining lamp as the light produced by the lamp will not be visible on the patient (the magnet is substantially transparent to the radiation, however). The presence of strong magnetic fields will mean that an electron beam is not an option.

A magnetic resonance image acquisition system can also be provided, to obtain information and derive an image of all or part of the target region within a patient on the patient support. A control means for the radiation source can then control the source so as to deliver a therapeutic radiation dose to a patient on the patient support, by receiving magnetic resonance images from the acquisition system during delivery of the dose.

The chassis is preferably rotatable continuously about the rotation axis.

A radiation detector can be mounted to the gantry opposite the source and adapted to quality assure the position of the leaves of the multi-leaf collimator, if desired.

The MLC will thus be fixed in its orientation, and may have a maximum field size that is small in the longitudinal direction (matched to the radiation window in the magnet, such as 15 cm at a radius of 60 cm) and large in the transverse direction. The MLC will not rotate, which will make the construction simpler and cheaper, and make the geometry more stable and easier to calibrate and QA.

The leaves may move only in the longitudinal direction. This makes the leaves short as they only have to traverse the small dimension of the collimator. As they are only moving a small distance, the tip of the leaf can have a large radius and thereby minimise the radiation penumbra. Also, moving in this direction facilitates target tracking as breathing is the main reason for movement, and is in a predominantly longitudinal direction. In addition, the lack of rotation and their particular longitudinal orientation means that the leaves of the MLC need not be driven against gravity, meaning the power requirements of the actuators are lessened.

To overcome the lack of rotational adjustment the leaves will have to be thinner than is generally the case, but guides can be provided. This together with modern IMRT and VMAT techniques will be able to produce equivalent dose distributions at the target. To prevent these thin leaves from bending under their own weight they can be supported across the treatment field. The additional material introduced by use of this support is insignificant compared to the material already in the magnet, which the beam must also pass through.

In another aspect, there is disclosed a method of operating a radiotherapy apparatus as described above. The method comprises the steps of: irradiating a target region of a patient on the patient support with a radiation beam; acquiring imaging data of the target region; and adapting the positions of the elongate leaves in dependence on the imaging data.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
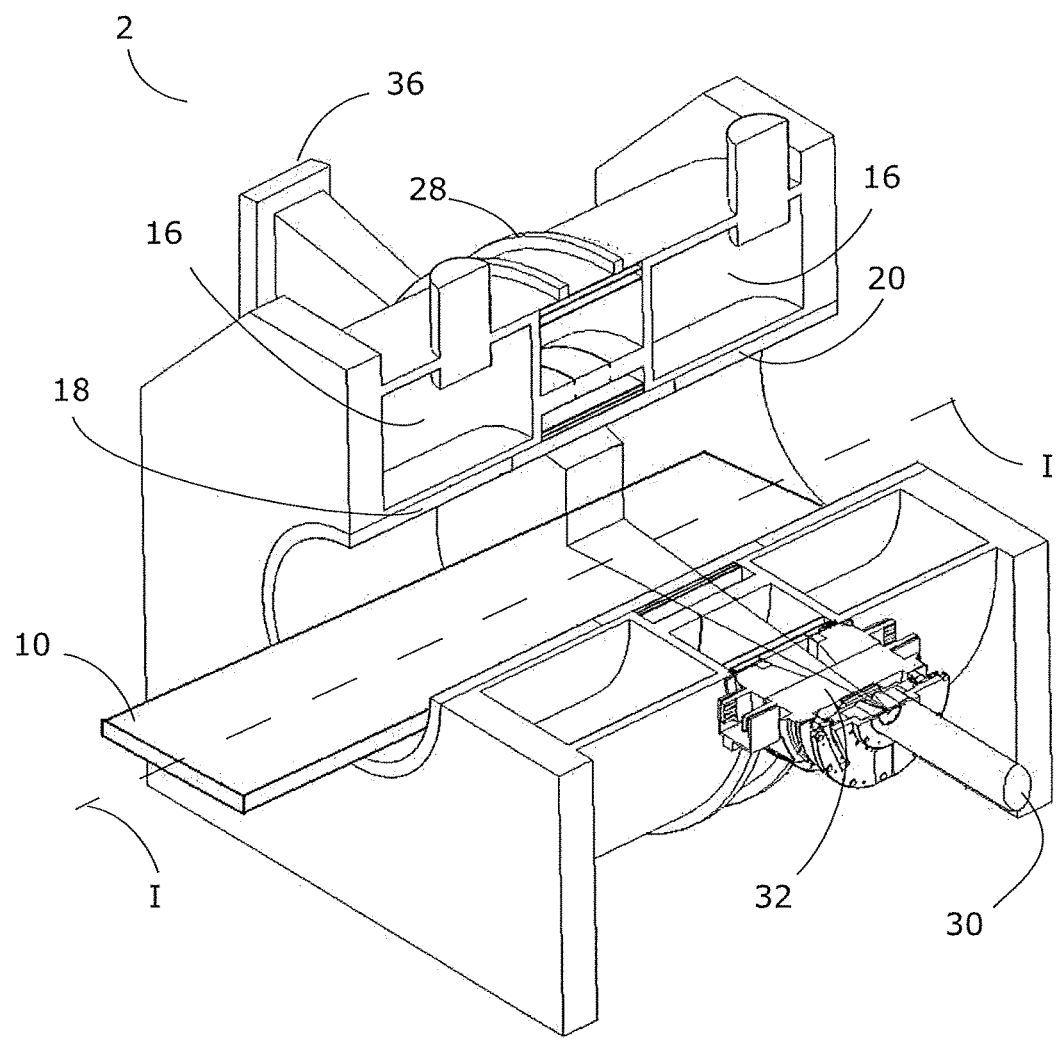
FIG. 1 shows a radiotherapy system according to embodiments of the present invention.
Figure 2:
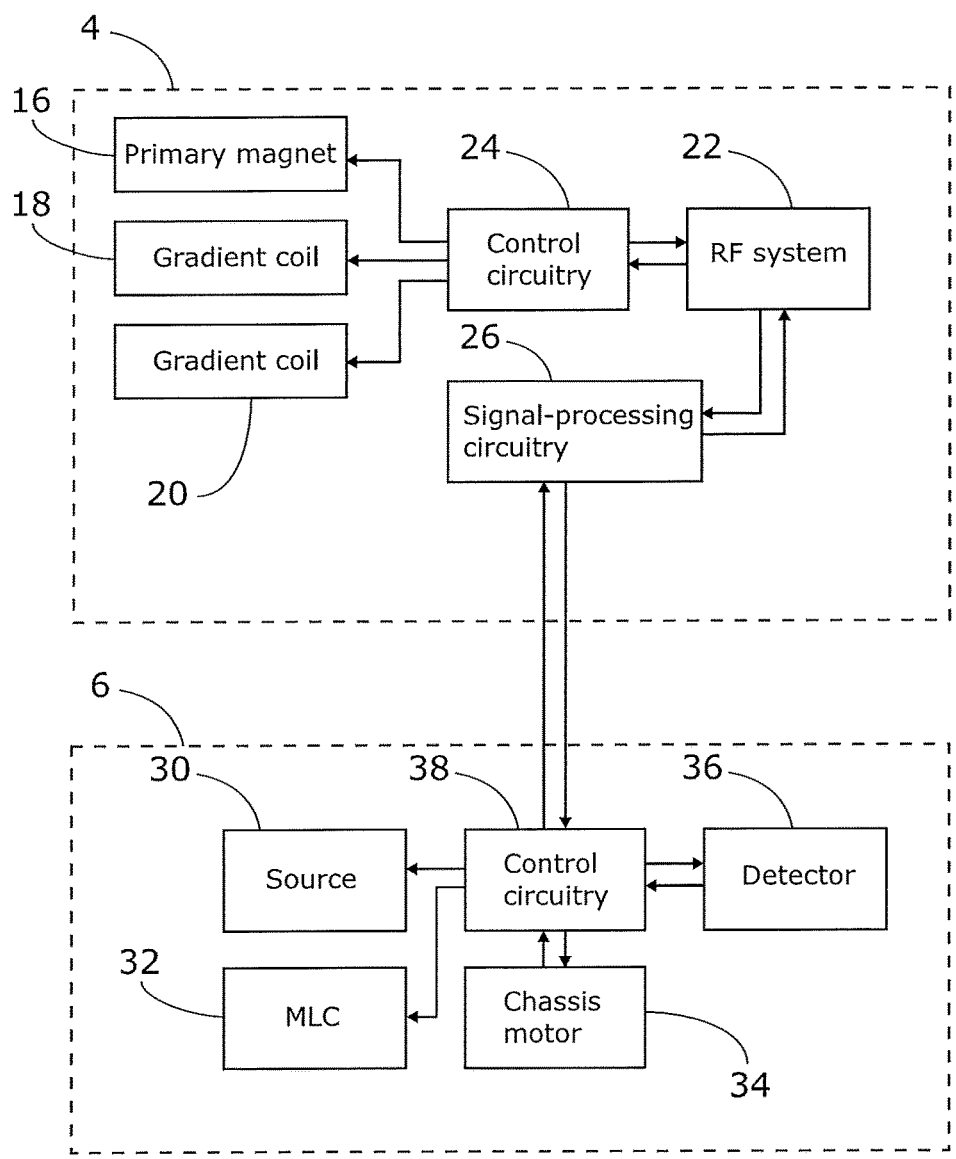
FIG. 2 is a schematic diagram of aspects of the radiotherapy system according to embodiments of the present invention.

FIG. 1 shows a system according to embodiments of the present invention, comprising a radiotherapy apparatus and a magnetic resonance imaging (MRI) apparatus. The radiotherapy apparatus 6 and MRI apparatus 4 are shown schematically in FIG. 2.

The system includes a couch 10, for supporting a patient in the apparatus. The couch 10 is movable along a horizontal, translation axis (labelled "I"), such that a patient resting on the couch is moved into the radiotherapy and MRI apparatus. In one embodiment, the couch 10 is rotatable around a central vertical axis of rotation, transverse to the translation axis, although this is not illustrated. The couch 10 may form a cantilever section that projects away from a support structure (not illustrated). In one embodiment, the couch 10 is moved along the translation axis relative to the support structure in order to form the cantilever section, i.e. the cantilever section increases in length as the couch is moved and the lift remains stationary. In another embodiment, both the support structure and the couch 10 move along the translation axis, such that the cantilever section remains substantially constant in length, as described in our U.S. patent application Ser. No. 11/827,320 filed on 11 Jul. 2007.

As mentioned above, the system 2 also comprises an MRI apparatus 4, for producing real-time imaging of a patient positioned on the couch 10. The MRI apparatus includes a primary magnet 16 which acts to generate the so-called "primary" magnetic field for magnetic resonance imaging. That is, the magnetic field lines generated by operation of the magnet 16 run substantially parallel to the central translation axis I. The primary magnet 16 consists of one or more coils with an axis that runs parallel to the translation axis I. The one or more coils may be a single coil or a plurality of coaxial coils of different diameter, as illustrated. In one embodiment, the one or more coils in the primary magnet 16 are spaced such that a central window of the magnet 16 is free of coils. In other embodiments, the coils in the magnet 16 may simply be thin enough that they are substantially transparent to radiation of the wavelength generated by the radiotherapy apparatus. The magnet 16 may further comprise one or more active shielding coils, which generates a magnetic field outside the magnet 16 of approximately equal magnitude and opposite polarity to the external primary magnetic field. The more sensitive parts of the system 2, such as the accelerator, are positioned in this region outside the magnet 16 where the magnetic field is cancelled, at least to a first order. The MRI apparatus 4 further comprises two gradient coils 18, 20, which generate the so-called "gradient" magnetic field that is superposed on the primary magnetic field. These coils 18, 20 generate a gradient in the resultant magnetic field that allows spatial encoding of the protons so that their position can be determined from the frequency at which resonance occurs (the Larmor frequency). The gradient coils 18, 20 are positioned around a common central axis with the primary magnet 16, and are displaced from one another along that central axis. This displacement creates a gap, or window, between the two coils 18, 20. In an embodiment where the primary magnet 16 also comprises a central window between coils, the two windows are aligned with one another.

An RF system 22 transmits radio signals at varying frequencies towards the patient, and detects the absorption at those frequencies so that the presence and location of protons in the patient can be determined. The RF system 22 may include a single coil that both transmits the radio signals and receives the reflected signals, dedicated transmitting and receiving coils, or multi-element phased array coils, for example. Control circuitry 24 controls the operation of the various coils 16, 18, 20 and the RF system 22, and signal-processing circuitry 26 receives the output of the RF system, generating therefrom images of the patient supported by the couch 10.

As mentioned above, the system 2 further comprises a radiotherapy apparatus 6 which delivers doses of radiation to a patient supported by the couch 10. The majority of the radiotherapy apparatus 6, including at least a source of radiation 30 (e.g. an x-ray source) and a multi-leaf collimator (MLC) 32, is mounted on a chassis 28. The chassis 28 is continuously rotatable around the couch 10 when it is inserted into the treatment area, powered by one or more chassis motors 34. In the illustrated embodiment, a radiation detector 36 is also mounted on the chassis 28 opposite the radiation source 30 and with the rotational axis of the chassis positioned between them. The radiotherapy apparatus 6 further comprises control circuitry 38, which may be integrated within the system 2 shown in FIG. 1 or remote from it, and controls the source the radiation source 30, the MLC 32 and the chassis motor 34.

The radiation source 30 is positioned to emit radiation through the window defined by the two gradient coils 18, 20, and also through the window defined in the primary magnet 16. According to embodiments of the present invention, the source 30 emits so-called "fan beams" of radiation. The radiation beam is collimated with appropriate shielding prior to arrival at the MLC 32, by which time it is already "letterbox-shaped" in order to pass through the MLC housing as described in greater detail below. That is, the radiation beam is relatively narrow in one dimension parallel to the axis of rotation of the chassis 28 (such as 15 cm at a radius of 60 cm), and is relatively wide in a dimension that is transverse to the axis of rotation of the chassis. Thus, the beam takes the fan shape that gives it its name. It is this fan-shaped beam that is ideally suited to the geometry of the system 2, in which two gradient coils 18, 20 are displaced from one another in order to allow the radiation access to the patient. A fan-shaped beam provides substantial radiation to the patient through the narrow window, meaning that the gradient coils 18, 20 can be placed closer together than with conventional integrated radiotherapy/imaging systems. This allows the gradient coils 18, 20 to generate stronger gradient fields than would otherwise be the case, increasing the quality of the images obtained by the MRI apparatus 4.

The radiation detector 36 is optimised for the geometry shown in FIG. 1, and can be used for QA and in-vivo dosimetry. The detector 36 is positioned outside the magnetic coils 16, 18, 20 on the chassis 28, aligned with the radiation beam exit. It therefore has a fixed position relative to the radiation source 30 and MLC 32.

Owing to the fact that it is outside the coils 16, 18, 20 the effect of scattered radiation will be dominated by the materials in the magnet 16, which are a constant and therefore comparatively easy to model. This is unlike existing electronic portal imaging device (EPID) schemes which are subject to varying scatter from the patient due to differing patient geometries which is difficult to predict.

Due to the large transverse size of the detector 36, it uses individual detector elements (not illustrated). These can either be diodes, ion chambers or similar. Because the detector 36 is used only for quality assurance (QA) and in-vivo dosimetry rather than patient imaging (the MRI apparatus 4 being the primary patient imager), the pitch of the detecting elements can be relatively coarse, i.e. substantially equal to the width of the leaves of the MLC 32 when projected onto the isocentric plane. The width of the leaves is defined by the design of the MLC and may be between 2 mm and 10 mm when projected onto the isocentric plane.

The detector 36 further comprises elements 52 to perform some of the machine QA on the MLC 32, i.e. detecting that the leaves of the MLC are correctly positioned. Columns of these detector elements will typically be at the pitch of the leaves of the MLC. There may be a number of columns of detector elements to allow the leaves to be detected at discrete positions (see FIG. 5). These columns of detector elements are ideally suited to an MLC which is fixed in its orientation, because the leaves will always be aligned to particular columns of detector elements.

In operation, a patient is placed on the couch 10 and the couch is inserted into the treatment area defined by the magnetic coils 16, 18 and the chassis 28. The control circuitry 38 controls the radiation source 30, the MLC 32 and the chassis motor to deliver radiation to the patient through the window between the coils 16, 18. The control circuitry 38 controls the source to deliver radiation in a fan beam, in the usual pulsed manner. The chassis motor 34 is controlled such that the chassis 28 rotates about the patient, meaning the radiation can be delivered from different directions. The MLC 32 is controlled to take different shapes, thereby altering the shape of the beam as it will reach the patient. Simultaneously with rotation of the chassis 28 about the patient, the couch 10 may be moved along a translation axis into or out of the treatment area (i.e. parallel to the axis of rotation of the chassis). With this simultaneous motion a helical radiation delivery pattern is achieved, known to produce high quality dose distributions.

The MRI apparatus 4, and specifically the signal-processing circuitry 26, delivers real-time (or in practice near real-time, after a delay in the order of milliseconds) images of the patient to the control circuitry 38. This information allows the control circuitry to adapt the operation of the source 30, MLC 32 and/or chassis motor 34, such that the radiation delivered to the patient accurately tracks the motion of the patient, for example due to breathing.

Figure 3:
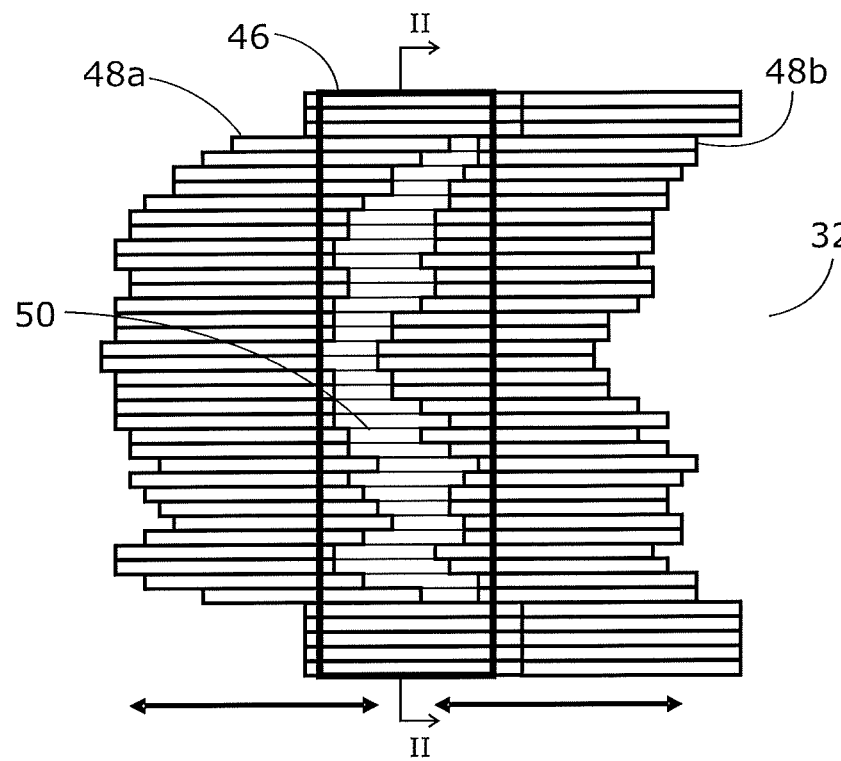
FIG. 3 shows a multi-leaf collimator according to embodiments of the present invention.

FIG. 3 shows an MLC 32 according to embodiments of the present invention.

The collimator 32 comprises a housing 46 which is effectively shaped as an elongate rectangular aperture. Pairs of leaves (for example as indicated with reference numerals 48a, 48b) are located along the housing 46, and are movable into and out of the aperture in a substantially continuous number of positions by action of a plurality of actuators. The actuators may be operated by electromagnetic motors, placed outside the coils 16, 18, 20 to minimize interference with the magnetic fields present in the MRI apparatus 4. At one extreme, each leaf may be positioned entirely outside the aperture; at the other, each leaf may be positioned entirely within the aperture. As illustrated, each leaf may be separately controllable to move into and out of the housing (i.e. the movement of the leaves in each pair is not linked). This embodiment allows the target region to be tracked more accurately, as it does not assume that the target is in the centre of the field of view.

The MLC 32 is fixed in its orientation and has a maximum field size defined by the shape of the housing 46 that is relatively small in the longitudinal direction (matched to the width of the gap between the two magnetic coils 18, 20, typically 15 cm at a radius of 60 cm) and relatively large in the transverse direction.

In one embodiment, the MLC 32 does not rotate. This makes the construction simpler and cheaper. It also makes the geometry more stable and easier to calibrate, and quality assurance easier to achieve. To overcome this lack of rotation, however, the leaves 48 are thinner than in conventional MLCs. To prevent these thin leaves from bending under their own weight they can be supported across the treatment field. The MLC 32 comprises a plurality of supports 50 that stretch across the housing, as shown most clearly in the cross-section view of FIG. 4. Each leaf 48 is shaped so that a relatively narrow portion slots between a pair of adjacent supports 50. Two shoulders are then defined between the relatively narrow region of each leaf and the relatively wide region, which sit on top of the supports 50. The provision of supports 50 is possible because there is no possibility of a field defining light in the MRI linac or the use of electrons, as the magnet 16 prevents it. The additional material introduced by use of the supports 50 can be insignificant compared to the material already in the magnet, and so does not further interfere with the therapeutic radiation delivered to the patient. For example, the leaves are typically manufactured from a material with a relatively high atomic number (e.g. tungsten) and represent a considerable barrier to the radiation due to their relatively thick cross section along the beam axis. In contrast, the supports 50 are relatively thin in that direction, and may be made from a material with a relatively low atomic number (e.g. aluminium). The combination of both these factors means that the supports 50 present a negligible barrier to the radiation, even though they are fixed across the beam's path. In alternative embodiments, a sheet of material (e.g. aluminium) may be placed over the exit to the MLC 32, in order to support the leaves. The sheet is again thin enough that it does not present a significant barrier to the radiation. The supports 50 may be grooves in the sheet, or raised projections extending from the sheet.

Figure 4:
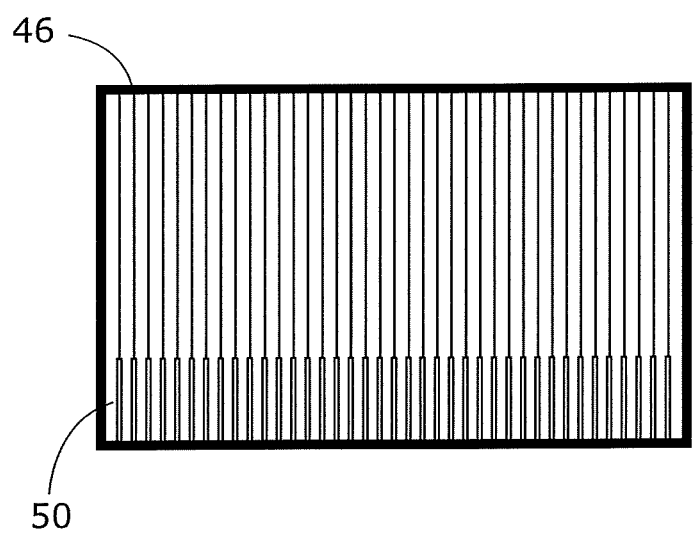
FIG. 4 is a cross-section view of the multi-leaf collimator shown in FIG. 3, along the line II.

Although not illustrated in FIG. 4, the leaves 48 may be thicker in parts further from the source of radiation 30 than parts nearer the source of radiation. That is, as the radiation beam diverges into the fan shape according to the present invention, so the leaves also increase in width so that the radiation beam is effectively blocked along the full length of the leaf 48.

The leaves 48 move only in the longitudinal direction. This makes the leaves short as they only have to traverse the small dimension of the collimator 32. As they are only moving a small distance the tip of each leaf can have a large radius and thereby minimise the radiation penumbra. Also, moving in this direction facilitates target tracking as targets generally move due to breathing and this is in a predominantly longitudinal direction.

Figure 5:
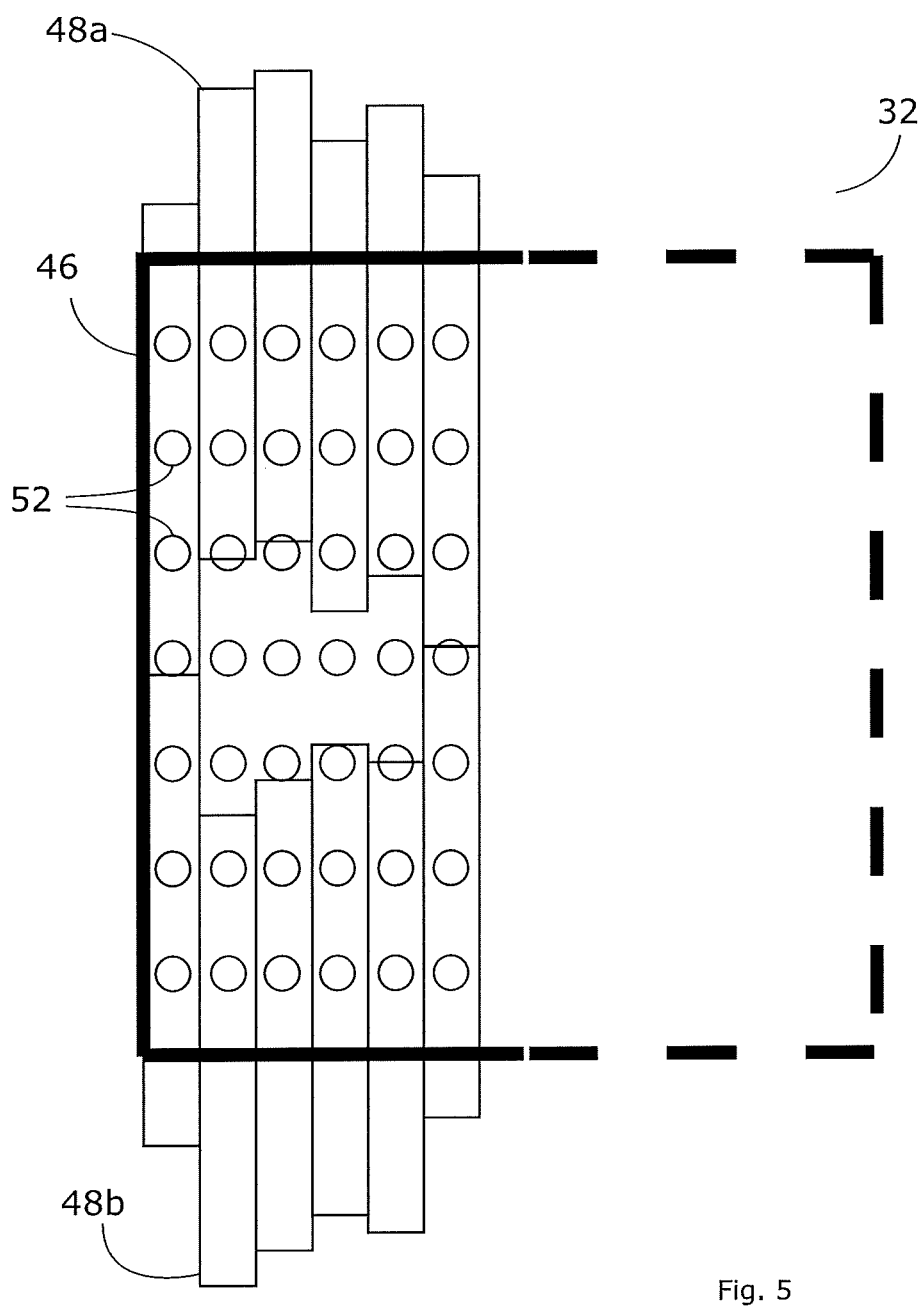
FIG. 5 shows a view of a multi-leaf collimator in which detector elements according to the embodiments of the present invention have been superimposed.

FIG. 5 shows a view of the multi-leaf collimator 32 on which detector elements 52 of the radiation detector 36 have been superimposed. Not all of the leaves 48 or detector elements 52 are shown for clarity. It can be seen that the detector elements 52 are arranged into columns which are aligned with the leaves 48 of the multi-leaf collimator. This allows detector 36 to perform quality assurance on the position of the leaves 48, but is generally insufficient for use as an imager of the region that is being targeted for therapy.

Figure 6:
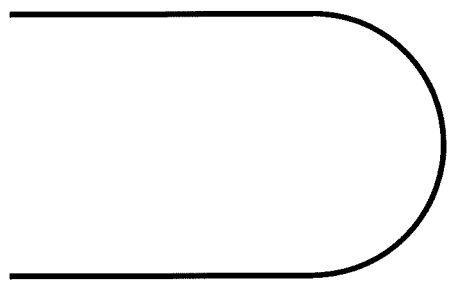
FIG. 6 shows the tip of a conventional leaf used in a multi-leaf collimator.
Figure 7:
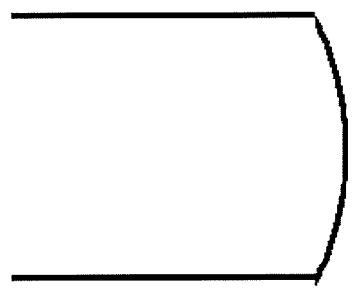
FIG. 7 shows the tip of a leaf according to an embodiment of the present invention.
Figure 8:
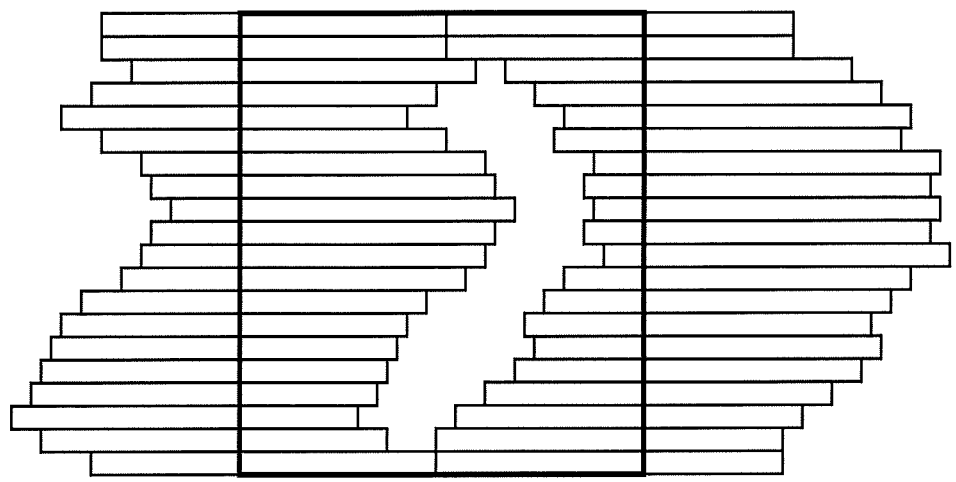
FIG. 8 shows a beam's eye view of a known multi-leaf collimator.
Figure 9:
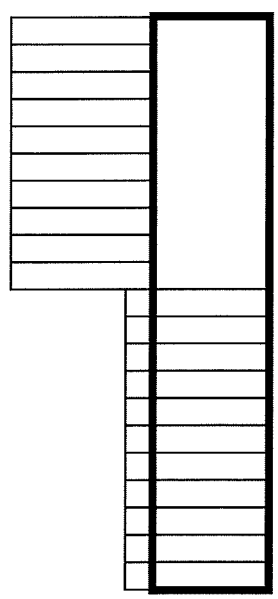
FIG. 9 shows a beam's eye view of another known multi-leaf collimator.

FIG. 6 shows the tip of a conventional leaf. It can be seen that the tip is relatively rounded. FIG. 7 shows the tip of a leaf according to embodiments of the present invention. The tip has a much larger radius (i.e. is flatter with sharper edges) due to the short range of travel of the leaves across the aperture. The latter tip creates a sharper definition between areas in which radiation is allowed to pass through the MLC 32, and areas where the radiation is blocked. This increases the accuracy with which radiation can be applied to the patient.

The present invention therefore provides a radiotherapy apparatus with a multi-leaf collimator. The radiotherapy apparatus comprises, in addition to a source of radiation, an image acquisition system comprising a plurality of magnetic coils. The multi-leaf collimator is adapted for use with this system by providing a plurality of leaves, each movable in between a withdrawn position in which the leaf lies outside the beam, an extended position in which the leaf projects across the beam and a plurality of intermediate positions therebetween. Moreover, the multi-leaf collimator is fixed in its orientation with respect to the source of radiation. It does not rotate with respect to the radiation source. This provides an apparatus that is more stable, and easier to calibrate and QA.

It will of course be understood that many variations may be made to the above-described embodiment without departing from the scope of the present invention.

Although the present invention has been described with reference to preferred embodiments, workers skilled in the art will recognize that changes may be made in form and detail without departing from the spirit and scope of the invention.

What is claimed is:

1. A radiotherapy apparatus comprising:
   a source of therapeutic radiation mounted on a chassis, the chassis being rotatable about a rotation axis and the source being adapted to emit a beam of radiation along a beam axis that intersects with the rotation axis, the beam of radiation directed through a multi-leaf collimator housing;
   a patient support;
   a set of magnetic coils, for establishing a magnetic field at a point of intersection of the beam axis and the rotation axis; and
   a multi-leaf collimator comprising the multi-leaf collimator housing shaped as an aperture through which the beam of radiation is directed, the multi-leaf collimator comprising a plurality of elongate leaves disposed with their longitudinal directions substantially aligned with a first direction and movable in that direction, the multi-leaf collimator being rotationally fixed in its orientation with respect to the source of radiation such that the elongate leaves are movable only in the first direction, wherein:
   the first direction is substantially parallel to the rotation axis, and wherein
   the set of magnetic coils are located on either side of the beam and are spaced from the point of intersection along the first direction,
   a thickness of a first portion of a first leaf of the plurality of elongate leaves is different from a second portion of the first leaf, the first portion being further from the source of therapeutic radiation than the second portion of the first leaf, the first and second portions of the first leaf being configured to move inside the aperture of the multi-leaf collimator housing through which the beam of radiation is directed, and the multi-leaf collimator comprises a plurality of supports within the multi-leaf collimator housing that extend across the beam inside the aperture for supporting the elongate leaves at least in their respective extended and intermediate positions.

2. The radiotherapy apparatus according to claim 1, wherein the first leaf varies in thickness such that, as the beam of radiation diverges into a fan shape, the first leaf increases in width to effectively block the beam of radiation along a full length of the first leaf.

3. The radiotherapy apparatus according to claim 2, in which the multi-leaf collimator comprises two banks of leaves, each extending from one side of the beam and moveable toward the other side, the extended position of each leaf being one in which the leaf concerned extends across substantially an entire width of the beam.

4. The radiotherapy apparatus according to claim 1, further comprising a magnetic resonance image acquisition system adapted to obtain information from an RF system in conjunction with the magnetic coils, and to derive an image of a patient on the patient support.

5. The radiotherapy apparatus according to claim 4, further comprising a control means for the radiation source adapted to control the source and the multi-leaf collimator so as to deliver a therapeutic radiation dose to a target region of the patient on the patient support, the control means being adapted to receive magnetic resonance images from the acquisition system during delivery of the dose.

6. The radiotherapy apparatus according to claim 1, wherein the chassis is continuously rotatable about the rotation axis, and wherein the elongate leaves are movable between respective withdrawn positions in which the leaves lie outside the beam.

7. The radiotherapy apparatus according to claim 1, further comprising a radiation detector mounted to a gantry opposite the source, wherein the patient support is movable along a translation axis, and wherein the translation axis, the rotation axis and the first direction are substantially parallel, the radiation detector comprising elements for detecting that the plurality of elongate leaves are correctly positioned, the elements being arranged in a plurality of columns to allow the plurality of elongate leaves to be detected at discrete positions.

8. A method of operating a radiotherapy apparatus, the radiotherapy apparatus comprising:
a source of therapeutic radiation mounted on a chassis, the chassis being rotatable about a rotation axis and the source being adapted to emit a beam of radiation along a beam axis that intersects with the rotation axis, the beam of radiation directed through a multi-leaf collimator housing;
a patient support;
a set of magnetic coils, for establishing a magnetic field at a point of intersection of the beam axis and the rotation axis; and
a multi-leaf collimator comprising the multi-leaf collimator housing shaped as an aperture through which the beam of radiation is directed, the multi-leaf collimator comprising a plurality of elongate leaves disposed with their longitudinal directions substantially aligned with a first direction and movable in that direction, the multi-leaf collimator being rotationally fixed in its orientation with respect to the source of radiation such that the elongate leaves are movable only in the first direction, wherein:
the first direction is substantially parallel to the rotation axis,
the set of magnetic coils are located on either side of the beam and are spaced from the point of intersection along the first direction,
a thickness of a first portion of a first leaf of the plurality of elongate leaves is different from a second portion of the first leaf, the first portion being further from the source of therapeutic radiation than the second portion of the first leaf, the first and second portions of the first leaf being configured to move inside the aperture of the multi-leaf collimator housing through which the beam of radiation is directed, and
the multi-leaf collimator comprises a plurality of supports within the multi-leaf collimator housing that extend across the beam inside the aperture for supporting the elongate leaves at least in their respective extended and intermediate positions, the method comprising:
acquiring imaging data of a target region; and
adapting positions of the elongate leaves in dependence on the imaging of the target region of a patient on the patient support with a therapeutic radiation beam.

9. The method according to claim 8, wherein the first leaf varies in thickness such that, as the beam of radiation diverges into a fan shape, the first leaf increases in width to effectively block the beam of radiation along a full length of the first leaf.

10. The method according to claim 8, further comprising:
rotating the chassis about the rotation axis, wherein the elongate leaves are movable between respective withdrawn positions in which the leaves lie outside the beam, wherein the patient support is movable along a translation axis, and wherein the translation axis, the rotation axis and the first direction are substantially parallel.

11. The radiotherapy apparatus according to claim 1, wherein the source of radiation is adapted to emit a beam of radiation towards the multi-leaf collimator, the beam received by the multi-leaf collimator having a first extent in the first direction, and a second, greater extent in a second direction normal to the first direction.

12. The method according to claim 8, wherein the source of radiation is adapted to emit a beam of radiation towards the multi-leaf collimator, the beam received by the multi-leaf collimator having a first extent in the first direction, and a second, greater extent in a second direction normal to the first direction.

13. The radiotherapy apparatus according to claim 1, wherein a tip of the first leaf is rounded and has first and second straight edges, wherein a first portion of the rounded tip of the first leaf is connected to the first straight edge, and wherein a second portion of the rounded tip of the first leaf is connected to the second straight edge, and wherein an intermediate portion between the first and second portions of the first leaf has a thickness that is greater than the thickness of the first portion of the first leaf and less than the thickness of the second portion of the first leaf.

14. The radiotherapy apparatus according to claim 1, wherein a thickness of the set of magnetic coils is determined based on a wavelength of the beam of radiation emitted by the source of therapeutic radiation.

15. The radiotherapy apparatus according to claim 1, wherein the source of therapeutic radiation emits the beam of radiation through a window defined by two gradient coils and a window defined by the set of magnetic coils.

16. The method according to claim 8, wherein a tip of the first leaf is rounded and has first and second straight edges, wherein a first portion of the rounded tip of the first leaf is connected to the first straight edge, wherein a second portion of the rounded tip of the first leaf is connected to the second straight edge, and wherein an intermediate portion between the first and second portions of the first leaf has a thickness that is greater than the thickness of the first portion of the first leaf and less than the thickness of the second portion of the first leaf.

17. The method according to claim 8, wherein a thickness of the set of magnetic coils is determined based on a wavelength of the beam of radiation emitted by the source of therapeutic radiation.

18. The method according to claim 8, wherein the source of therapeutic radiation emits the beam of radiation through a window defined by two gradient coils and a window defined by the set of magnetic coils.

\* \* \* \* \*